United States Patent
Martin

(10) Patent No.: US 9,433,643 B2
(45) Date of Patent: Sep. 6, 2016

(54) MICROBICIDAL COMPOSITION COMPRISING HYDROGEN PEROXIDE AND AMINOCARBOXYLIC ACIDS

(71) Applicant: Roy W. Martin, Downers Grove, IL (US)

(72) Inventor: Roy W. Martin, Downers Grove, IL (US)

(73) Assignee: Truox, Inc., McClellan, CA (US)

( * ) Notice: Subject to any disclaimer, the term of this patent is extended or adjusted under 35 U.S.C. 154(b) by 0 days.

(21) Appl. No.: 14/120,089

(22) Filed: Apr. 24, 2014

(65) Prior Publication Data

US 2014/0322349 A1    Oct. 30, 2014

Related U.S. Application Data

(60) Provisional application No. 61/854,728, filed on Apr. 30, 2013.

(51) Int. Cl.
| | |
|---|---|
| *A61K 33/40* | (2006.01) |
| *A01N 37/16* | (2006.01) |
| *A01N 37/44* | (2006.01) |
| *A01N 59/00* | (2006.01) |

(52) U.S. Cl.
CPC ............... *A61K 33/40* (2013.01); *A01N 37/16* (2013.01); *A01N 37/44* (2013.01); *A01N 59/00* (2013.01)

(58) Field of Classification Search
CPC .................................................... A01N 37/16
See application file for complete search history.

(56) References Cited

U.S. PATENT DOCUMENTS

| 5,914,303 | A | * | 6/1999 | Sankey | C11D 3/3945 252/186.1 |
|---|---|---|---|---|---|
| 6,096,348 | A | | 8/2000 | Miner et al. | |
| 6,627,657 | B1 | * | 9/2003 | Hilgren | A01N 37/16 514/553 |
| 7,354,604 | B2 | | 4/2008 | Ramirez et al. | |
| 7,658,953 | B2 | | 2/2010 | Bobbert | |
| 8,110,538 | B2 | | 2/2012 | Martin et al. | |
| 2006/0198876 | A1 | * | 9/2006 | Tichy | C11D 17/049 424/443 |
| 2006/0199752 | A1 | * | 9/2006 | Tichy | A01N 59/00 510/375 |
| 2011/0014276 | A1 | | 1/2011 | Karagoezian | |
| 2013/0251590 | A1 | * | 9/2013 | Golden | A01N 59/00 422/24 |

FOREIGN PATENT DOCUMENTS

EP    1001012    *    5/2000

OTHER PUBLICATIONS

U.S. Appl. No. 13/066,226, filed Apr. 8, 2011, Roy W. Martin.

* cited by examiner

*Primary Examiner* — David J Blanchard
*Assistant Examiner* — Sarah Alawadi

(57) ABSTRACT

The invention relates to a microbicidal composition comprising hydrogen peroxide, peroxycarboxylic acid, and aminocarboxylic acid. The hydrogen peroxide and peroxycarboxylic acid form associations with the aminocarboxylic acid that enhances the microbicidal efficacy of the composition. The invention further discloses methods for its use.

6 Claims, 1 Drawing Sheet

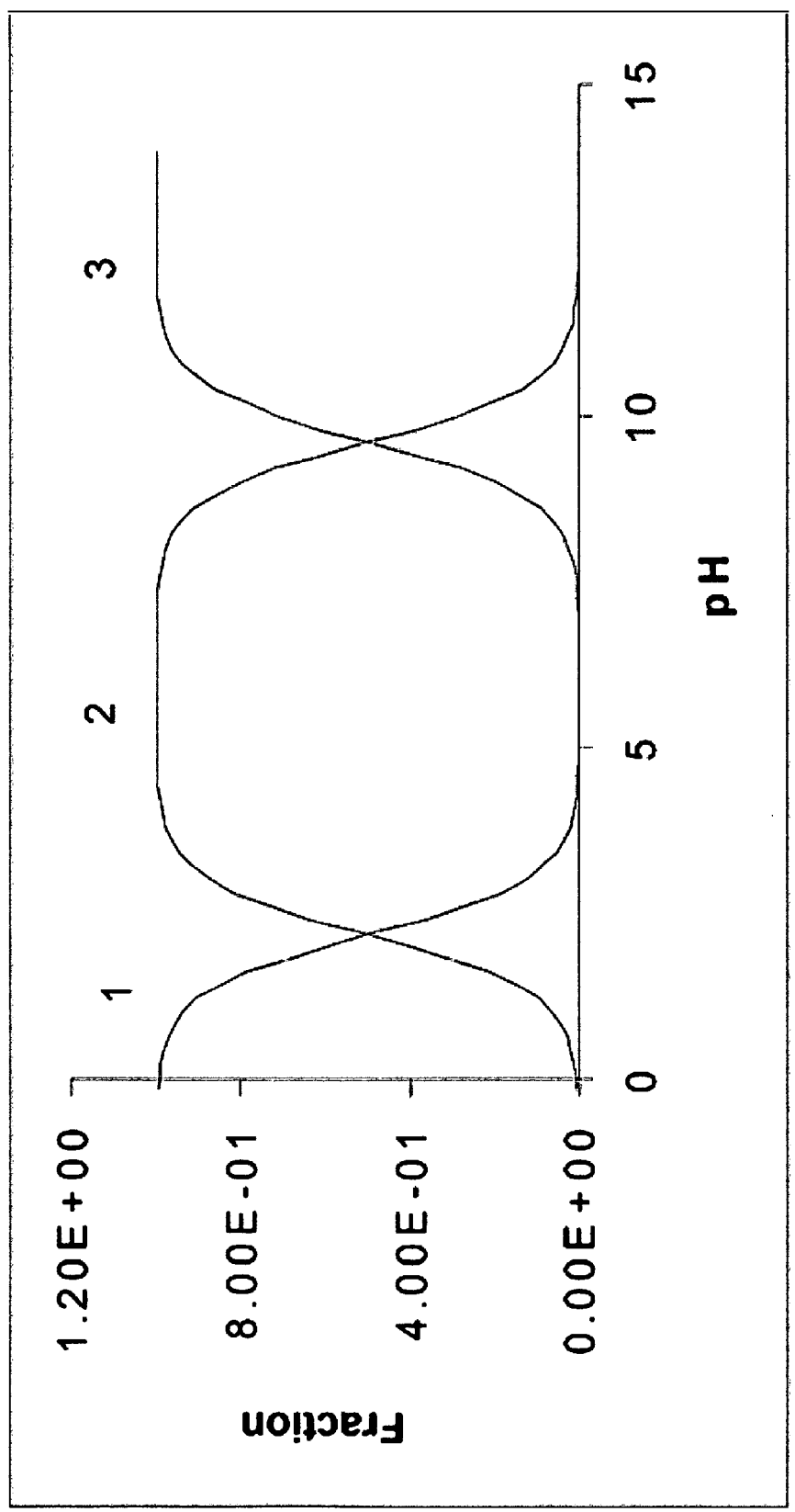

MICROBICIDAL COMPOSITION COMPRISING HYDROGEN PEROXIDE AND AMINOCARBOXYLIC ACIDS

FIELD OF THE INVENTION

The present invention relates to a microbicidal composition comprising an aqueous solution of hydrogen peroxide, peroxycarboxylic acid and aminocarboxylic acids with enhanced microbicidal efficacy including endospores and mycobacterium.

BACKGROUND TO THE INVENTION

In infection control practice spores (endospores) are typically used as the benchmark for evaluating the potency of a disinfectant. If a chemical disinfectant is effective in destroying spores, then it will be judged effective for use as a hard surface disinfectant, against all possible bacterial species and lipophilic and hydrophilic viral particles.

Very few liquid chemical disinfectants are effective sporicides, particularly in cold soaking instruments sensitive to chemical attack. The most widely used sporicidal chemical solutions are based on aldehydes, short chain alcohols, phenolic compounds, and certain peroxygens. Aldehydes (e.g. formaldehyde and glutaraldehyde), although highly effective, suffer from serious occupational safety and environmental disposal hazards. Of the peroxygens, peracids are those most widely used in liquid form. Peracetic and performic acids have been marketed for the disinfection of semicritical and critical instruments; however, their aggressive chemical nature tend to damage surfaces and instruments with prolonged use.

Alcohol or phenolic compounds which exhibit good efficacy against mycobacterial species are typically not effective in destroying bacterial endospores. Mycobactericidal products that are based on short-chain alcohols typically contain these ingredients at high concentrations (usually higher than 20% w/w). Furthermore, they are often characterized by a strong alcoholic odor and are therefore difficult to use in large quantities in small enclosed spaces by chemically sensitive individuals. Phenolic compounds can be used by themselves or in combination with other germicidal actives (such as with quaternary ammonium compounds and solvents), in order to achieve wide spectrum efficacy.

Hypochlorite solutions and other chlorine-based compounds are effective against both mycobacteria and bacterial endospores; however, they are easily inactivated by the presence of organic matter, are unstable when diluted, have a strong, objectionable, chlorinated smell, and are highly corrosive and therefore damaging to most instruments and surfaces.

Aqueous chemical disinfectants are used in applications where, due to occupational, environmental, or toxicological concerns, solvent-based solutions cannot be used. While there are a large number of disinfecting and sanitizing solutions available in the marketplace, there is still a need for a low-volatility, low toxicity, non-corrosive, non-irritating, and stable aqueous disinfectant which is effective against hydrophilic viruses, acid-fast bacteria and bacterial endospores.

Furthermore, embodiments of the invention are well suited for use in food intervention to reduce the potential of contamination of food product by food-borne pathogens.

The present invention is intended to at least partially address these needs.

SUMMARY OF THE INVENTION

The disinfecting solutions of the present invention provides in accordance with a first aspect, a microbicidal composition comprising:

A microbiocidal composition in the form of an aqueous solution comprising: an aqueous solution of hydrogen peroxide in a concentration from 3% to 6% by weight; an association forming concentration of alpha aminocarboxylic acid; peroxycarboxylic acid in a concentration from 0.05% to 1% by weight; a phosphate ester comprising a hydrophilic polyoxyethylene chain having a range of PEO-3 to PEO-9 and an R-terminal group selected from the group consisting of a lipophilic alkyl chain having a range of C9 to C13 and a nonylphenol, and in a concentration from 0.05% to 1% by weight; the pH of the aqueous solution being less than the isoelectric point of the alpha aminocarboxylic acid; and wherein the alpha aminocarboxylic acid forms associations with at least one of peroxycarboxylic acid and hydrogen peroxide, said associations enhance the microbicidal efficacy of the composition.

Aminocarboxylic acids comprise zwitterionic compounds having an amine functional group bonded to the alpha carbon of a carboxylic acid and have the general structure:

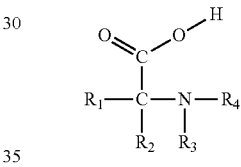

Wherein $R_1$, $R_2$, $R_3$, and $R_4$ comprise hydrogen (H) or carbon (C).

The aminocarboxylic acids comprise zwitterionic compounds having an amine functional group attached to the alpha carbon of a carboxylic acid. The aminocarboxylic acids structure substantially increases the electronegativity to the corresponding carboxylic acid group reducing the pKa value of the carboxylic acid group to less than 3.0. The aminocarboxylic acids comprise a carboxylic acid having a carbon based backbone ranging from $C_1$ to $C_6$. The carbon based backbone may comprise an aliphatic or cyclic structure. The carbon based backbone of the aminocarboxylic acids can be substituted with other groups. Non-limiting examples of substitution groups include alkyl, aryl, cyclic, heterocyclic, halo, amine, nitro, keto, carboxyl, and hydroxyl. The molecular mass of the aminocarboxylic acids is preferably less than 200 to enhance its penetration of membranes of microbiological organisms. Non-limiting examples of aminocarboxylic acids include: glycine, alanine, arginine, lysine, aspartic, glutamic, serine, threonine, valine, isoleucine, leucine, phenylalanine, tyrosine, and proline.

The peroxycarboxylic acid is selected from at least one $C_1$ to $C_{21}$, carbon based peroxycarboxylic acids and aminoperoxycarboxylic acids.

Aminoperoxycarboxylic acids comprise the equilibrium products resulting from the reaction between hydrogen peroxide and at least one aminocarboxylic acid and aminocarboxylic acid precursors. Non-limiting examples of aminocarboxylic acid precursors include aminocarboxylic anhydrides, amino aldehydes, and amino acyl chlorides.

Non-limiting examples of aminoperoxycarboxylic acids include aminoperoxyethanoic acid and 2-aminoperoxypropanoic acid.

The $C_1$ to $C_{21}$ carbon based peroxycarboxylic acids may be aliphatic or cyclic carbon structures. Non-limiting examples of $C_1$ to $C_{21}$ carbon based peroxycarboxylic acids include: peroxyacetic acid, peroxybutanoic acid, peroxypentanoic acid, peroxysuccinic acid, peroxybenzoic acid, peroxyoctanoic acid, peroxyadipic acid, peroxydodecanoic acid, and peroxydecanoic acid.

Additionally, the solution may comprise at least one fragrance in a concentration of from 0.01 to 4% w/w, all based on the total weight of the solution. At least one component may be present in a concentration of from 0.1 to 2.5% w/w, or from 0.25 to 1.0% w/w, or 0.4 to 0.6% w/w, based on the total weight of the solution. The fragrance is preferably myrcenol.

To achieve the desired pH values, the solution may contain acid or alkaline buffers exemplified by the non-limiting examples phosphoric acid, citric acid, glycolic acid, lactic acid, acetic acid, sodium carbonate, calcium carbonate, sodium carbonate, potassium hydroxide, sodium hydroxide, and ethanolamine.

In one embodiment, the solution may further comprise at least one nonionic surfactant in a concentration of from 0.005 to 3% w/w, preferably from 0.01 to 3% w/w, more preferably from 0.02 to 1% w/w, and even more preferably from 0.04 to 0.06% w/w, based on the total weight of the solution. Furthermore, the at least one nonionic surfactant is preferably chosen from (a) ethoxylated alcohols and alkylglycosides having a hydrophile lypohile balance from 5 to 15, which may be a C6-C10 alkyl, 3-9 moles of ethylene oxide (EO) alcohol ethoxylate; and (b) a sufficiently water-soluble block copolymer of ethylene oxide or propylene oxide.

In yet another embodiment, the solution may further comprise at least one cation sequestering agent in a concentration of from 0.01 to 6% w/w, preferably from 0.05 to 2% w/w, more preferably from 0.1 to 2% w/w, and even more preferably from 0.5 to 1% w/w, based on the total weight of the solution. The cation sequestering agent may be 1-hydroxyethylidene-1,1-diphosphonic acid.

In still another embodiment of the invention, the solution may contain at least one anionic surfactant chosen from (a) C8-C16 alkyl benzene sulfonic acids and alkali metal, alkaline earth metal, ammonium or alkylamine salts thereof; (b) C8-C18 alkyl sulfonic acid; (c) C8-C16 alkyl sulfates; and (d) C6-C12 alkyl diphenyl oxide sulfonate surfactants, in a concentration of from 0.01 to 10% w/w, or from 0.01 to 6% w/w, 0.01 to 5% w/w, 0.01 to 3% w/w, or 0.05 to 1% w/w, based on the total weight of the solution. The at least one anionic surfactant may be an alkyl benzene sulfonic acid and, preferably, dodecyl benzene sulfonic acid.

In an embodiment suitable for inactivating resistant, hydrophilic viruses, the solution may further comprise a C6-C12 alkyl diphenyl oxide sulfonate surfactant in a concentration of from 0.01 to 5% w/w, 0.05 to 3% w/w, 0.05 to 2% w/w, or from 0.05 to 1.5% w/w, based on the total weight of the solution. The surfactant may be a C10 alkylated sulfonated diphenyl oxide sodium salt.

Solutions according to the present invention may comprise at least one corrosion inhibitor in a concentration of from 0.001 to 15% w/w, 0.001 to 5% w/w, 0.01 to 1% w/w, 0.01 to 0.5% w/w, or 0.02 to 0.22% w/w, based on the total weight of the solution. The at least one corrosion inhibitor may be chosen from 1,2,3 benzotriazole, sodium molybdate, sodium nitrite, sodium bisulfate, sodium metabisulfate, chromates, borates, phosphates, polyphosphates, sodium benzoate, sodium silicate, sodium gluconate, and a film forming composition. The preferred film forming composition comprises a hydrotrope with at least one of: polyvinylpyrrolidone; and ethoxylated alcohols having 3-6 moles of ethylene oxide (EO) alcohol ethoxylate. Desirable hydrotropes may be selected from: sodium xylene sulfonate; a phosphate ester comprising (a) a hydrophilic polyoxyethylene chain having a range of PEO-3 to PEO-12 and an R-terminal group selected from the group consisting of a lipophilic alkyl chain having a range of C9 to C13 and a nonylphenol; (b) ethoxylated polyarylphenol phosphate having a polyoxyethylene chain of POE-16; (c) and a phosphate ester comprising an alkylphenoxy polyethoxyethanol.

The solution may further contain a hydrotrope in a concentration of from 0.01 to 15% w/w, based on the total weight of the solution. Non-limiting examples of suitable hydrotropes include sodium xylene sulfonate, a phosphate ester comprising (a) a hydrophilic polyoxyethylene chain having a range of PEO-3 to PEO-9 and an R-terminal group selected from the group consisting of a lipophilic alkyl chain having a range of C9 to C13 and a nonylphenol; (b) ethoxylated polyarylphenol phosphate having a polyoxyethylene chain of POE-16; (c) a phosphate ester comprising an alkylphenoxy polyethoxyethanol; and C6 alkyl diphenyl oxide sulfonate surfactant.

The solution may further contain a nonionic polymer in a concentration of from 0.01 to 15% w/w, based on the total weight of the solution. A preferred nonionic polymer comprises polyvinylpyrrolidone.

Furthermore, the solution may include from 0.1 to 20% w/w of a solvent such as a glycol or glycol ether (e.g. propylene glycol).

The water used in solutions according to the invention may be tap water, deionized water, or a mixture thereof.

The invention provides, in accordance with a second aspect, a concentrated aqueous, acidic solution which may be diluted with water to provide a solution according to the first aspect of the invention. Such solution may have a total hydrogen peroxide of up to 30% w/w, based on the total weight of the solution.

The invention provides, in accordance with a third aspect, a method for killing microbiological organisms embedded in dried soil deposits, said method comprising the steps of: forming a composition in the form of an aqueous solution comprising; an aqueous solution of hydrogen peroxide in a concentration from 3% to 6% by weight, an association forming concentration of glycine, peroxyacetic acid in a concentration from 0.05% to 1% by weight, a phosphate ester comprising a hydrophilic polyoxyethylene chain having a range of PEO-3 to PEO-9 and an R-terminal group selected from the group consisting of a lipophilic alkyl chain having a range of C9 to C13 and a nonylphenol and in a concentration from 0.05% to 1% by weight, the pH of the aqueous solution being adjusted as needed to less than the isoelectric point of the alpha aminocarboxylic acid; and applying the composition to said deposits.

In accordance with the fourth aspect, the invention provides a disposable fabric wipe that is impregnated with the solution or composition according to first aspect of the invention. The wipes provide for a convenient means of delivering a disinfecting concentration of the disinfecting solution as well as mechanical cleaning (wiping) of the surface. After cleaning the surface with the fabric wipe, the wipe can be discarded.

In accordance with the fifth aspect, the invention provides a composition comprising peroxyacetic acid with enhanced equilibrium resulting in elevated peroxyacetic acid activity in the disinfecting solution.

Peroxyacetic acid solutions comprises an equilibrium product according to the following equation:

$$H_2O_2 + CH_3CO_2H \leftrightarrow CH_3CO_3H + H_2O$$

The equation illustrates that when peroxyacetic acid (PAA) is in a concentration greater than the equilibrium concentration for a given solution, the concentration of PAA will be reduced to establish equilibrium by reverting PAA back to acetic acid (parent carboxylic acid) and hydrogen peroxide.

It has been discovered that the equilibrium of peroxyacetic acid solution can be altered in favor of retaining (preserving) elevated concentrations of peroxyacetic acid in a solution that otherwise would have an equilibrium comprising a concentration of PAA at least 50% lower than the initial concentration of PAA. Furthermore, it has been discovered that replacing or supplementing a portion of acetic acid with aminoethanoic acid substantially reduces the acetic acid odor while preserving at least 25% higher concentration of peracetic acid.

DESCRIPTION OF THE FIGURES

FIG. 1 illustrates the fraction of the major microscopic species of glycine as a function of pH. The number on the top of each curve corresponds to the microscopic species: 1 is positively charged; 2 is the zwitterion; and 3 the negatively charged species.

TESTING

Solution A

To a 500 ml flask with magnetic stirring rod, 24 ml of 50% $H_2O_2$ was combined with 93 ml of distilled water and 3 ml of 98% $H_2SO_4$ while mixing. 10.75 ml of succinic anhydride was added and allowed to react at ambient temperature for 6 hours while covered. 162 ml of distilled water was added to the mixture followed by 3 grams of glycine. The mixture was allowed to mix for about 30 minutes. 360 µl of Stepfac 8180 was added followed by about an hour of mixing to form a homogenous solution.

Solution B-C

To a 1000 ml flask with magnetic stirring rod, 48 ml of 50% $H_2O_2$ was combined with 186 ml of distilled water and 6 ml of 98% $H_2SO_4$ while mixing. 26.6 ml of acetic anhydride was added and allowed to react at ambient temperature for 6 hours while covered. 329 ml of distilled water was added to the mixture.

The stock solution was separated equally by weight (approx 300 gm) into 2-separate 500 ml flask.

Solution B was prepared by addition of 3 grams of glycine ($H_2O_2$ to glycine molar ratio of 8.8:1 respectively) and mixed until clear followed by 360 µl of Stepfac 8180.

Solution C was prepared by addition of 6.6 grams of glycine ($H_2O_2$ to glycine molar ratio of 4:1 respectively). The mixture was allowed to mix for about 30 minutes. 360 µl of Stepfac 8180 was added followed by about an hour of mixing to form a homogenous solution.

Testing Solutions A, B, C against *B. subtilis* Suspension

In this test 1.0 ml of bacterial culture (*B. subtilis* spore culture) was added to 9.0 ml of disinfectant solution at 20±1° C. and mixed. After 1.0, 2.0, 3.0 5.0, and 10.0 minutes of exposure at 20±1° C., 1.0 ml was transferred from the reaction tube into 19 ml of neutralizing recovery medium (NRM). Serial ten-fold dilutions were made as 1.0 ml into 9 ml portions of neutralizing recovery medium. One half (0.5) ml portions of each dilution were placed onto the surface of nutrient agar (NA) in petri plates. The first neutralizer tube (19 ml NRM+1 ml culture/disinfectant solution suspension) was filtered through a 0.45 µm membrane filter and rinsed with approximately 50 ml of sterile deionized water and the filter was transferred onto the surface of NA in a petri plate. Plates were incubated at 35±2° C. for ≥24 hours. Surviving colonies were counted and multiplied by appropriate dilution factors to determine the number of surviving colony forming units (CFU) of *B. subtilis* spores that remained in the reaction tube at each exposure time for each disinfectant solution.

Results

| Disinfectant | Exposure Time (min) | Surviving CFU | $Log_{10}$ Reduction |
|---|---|---|---|
| A | 1.0 | $3.44 \times 10^4$ | 3.48 |
|   | 2.0 | 0 | 8.02 |
|   | 3.0 | 0 | 8.02 |
|   | 5.0 | 0 | 8.02 |
|   | 10.0 | 0 | 8.02 |
| B | 1.0 | 0 | 8.02 |
|   | 2.0 | 0 | 8.02 |
|   | 3.0 | 0 | 8.02 |
|   | 5.0 | 0 | 8.02 |
|   | 10.0 | 0 | 8.02 |
| C | 1.0 | 0 | 8.02 |
|   | 2.0 | 0 | 8.02 |
|   | 3.0 | 0 | 8.02 |
|   | 5.0 | 0 | 8.02 |
|   | 10.0 | 0 | 8.02 |

Disinfectant solution A killed 3.48 $log_{10}$ of *B. subtilis* spores in 1 minute with total kill (8.02 $log_{10}$) within 2 minutes. Disinfectant solutions B and C killed all *B. subtilis* spores (8.02 $log_{10}$) in suspension in 1 minute.

Testing Solutions A, B, C Against *S. aureus* Suspension

In this test 1.0 ml of bacterial culture (*S. aureus*) was added to 9.0 ml of disinfectant solution at 20±1° C. and mixed. After 0.5, 1.0, 2.0, and 5.0 minutes of exposure at 20±1° C., 1.0 ml was transferred from the reaction tube into 19 ml of neutralizing recovery medium (NRM). Serial ten-fold dilutions were made as 1.0 ml into 9 ml portions of neutralizing recovery medium. One half (0.5) ml portions of each dilution were placed onto the surface of nutrient agar (NA) in petri plates. The first neutralizer tube (19 ml NRM+1 ml culture/disinfectant solution suspension) was filtered through a 0.45 µm membrane filter and rinsed with approximately 50 ml of sterile deionized water and the filter was transferred onto the surface of NA in a petri plate. Plates were incubated at 35±2° C. for ≥24 hours. Surviving colonies were counted and multiplied by appropriate dilution factors to determine the number of surviving colony forming units (CFU) of *S. aureus* that remained in the reaction tube at each exposure time for each disinfectant solution.

Results

Disinfectant solutions A, B, and C killed all *S. aureus* (7.78 $log_{10}$) in suspension in 0.5 minutes.

*Bacillus subtilis* Carrier Test

The disinfecting solutions were test using methods of ASTM E2197-11 Standard Quantitative Disk Carrier Test Modified for Glass Surfaces Using *B. subtilis* to determine the sporicidal efficacy of the microbicidal compositions.

Solution D

A stock solution of peroxyacetic acid (PAA) was prepared by combining 8 ml of 50% $H_2O_2$ and 8 ml of acetic anhydride while mixing. The reaction was allowed to proceed at ambient temperature for 6 hours while covered.

To 1000 ml flask, 32 ml of 50% $H_2O_2$, 300 ml distilled water, 10 ml of stock PAA solution, 1.6 ml of 98% H2SO4, and 18 grams of glycine ($H_2O_2$ to glycine molar ratio of 2:1 respectively) were added and mixed for about 60 minutes. Another 37 ml of distilled water was added and allowed to mix for about 5 minutes. 400 µl of Stepfac 8180 was added and allowed to mix for about 60 minutes. The sample was tested using an FMC peroxyacetic acid test kit providing over 6000 ppm as PAA. The sample was again tested after 7 days of storage providing over 6000 ppm as PAA, showing no detectable loss of PAA.

Preparation of Bacterial Spore Culture

*Bacillus subtilis* ATCC#6633 was obtained fresh from the American Type Culture Collection within twelve months of this test. *B. subtilis* was maintained on nutrient agar (NA) slants at 3±2° C. after monthly transfers to fresh nutrient agar slants which were grown for 48±8 hours at 35±2° C. *B. subtilis* Sporulation Medium was prepared by dissolving 10 g Tryptone+10 g NaCl+5 g Yeast Extract+20 g Bacto Agar+2 ml 0.01M $MnCl_2$ in 1 L DIW. Portions of 300 ml were dispensed into a baking dish, covered with foil, and steam sterilized for 20 minutes at 121° C. A $CaCl_2$ solution was prepared at 0.1 g/ml, filter sterilized, and 0.6 ml $CaCl_2$ solution was aseptically added to 300 ml sterilized agar. The agar was gently mixed and allowed to solidify. From the stock culture of *B. subtilis*, one loopful was inoculated onto a NA slant and incubated for 3 days 35±2° C. This culture was then re-suspended in 3 ml of sterile saline solution and used to inoculate a lawn of *B. subtilis* sporulation medium in an 8 in×8 in Pyrex baking dish. The culture was spread over the surface of the agar, covered with aluminum foil, and incubated for seven days at 35±2° C. After incubation, 25 ml of sterile saline were added to the lawn and the bacterial culture was gently scraped from the agar with a sterile rubber policeman to suspend in the saline. The culture was collected, homogenized with 5 to 10 slow twisting strokes in a 40 ml Ten-Broeck tissue homogenizer, and transferred to a sterile bottle. Twenty-five (25) ml of 99% isopropanol were added to the culture and the culture was stored in the refrigerator at 3±2° C. The culture was diluted ten-fold into sterile saline for use in this study.

The ten-fold diluted culture was washed three times by centrifuge and re-suspended in phosphate buffered saline (PBS) before use in the study.

Prepare Soil Load and Inoculum

The soil load consisted of a mixture of the following stock solutions in phosphate buffered saline (PBS):
 a. 0.5 g Tryptone in 10 ml PBS
 b. 0.5 g Bovine Serum Albumin (BSA) in 10 ml PBS
 c. 0.04 g Bovine Mucin in 10 ml PBS Solutions were prepared separately and sterilized by passage through a 0.2 µm syringe filter. To obtain 5.0 ml of inoculum, 250 µl BSA, 1.0 ml mucin, and 350 µl tryptone were added to 3.4 ml microbial suspension.

Prepare Carriers

New glass cover slips were rinsed once with deionized water (DIW), three times with 95% ethanol, and finally rinsed three times with DIW. The glass cover slips were thoroughly dried with paper towels, placed in a glass beaker, and steam sterilized for 20 minutes at 121° C. The glass cover slips were then placed into sterile petri plates.

Inoculate and Dry the Carriers

The inoculum was mixed on a vortex mixer to evenly distribute the cells. Using a micro-pipettor, 10 µl was withdrawn and placed at the center of each sterilized glass cover slip without spreading. For consistency, the same pipettor tip was used for all carrier inoculations. The petri plates containing inoculated carriers were capped with lids and placed into a desiccator jar over Drierite. A vacuum was pulled on the jar at 20-25 in. Hg for 20 minutes. The carriers were held in the jar for at least 2 hours at ambient temperature to dry. At the end of the drying period, plates were carefully removed from the jar and carriers were discarded if the inoculum had run off the side. The carriers were then ready for use in the test.

Determine the Original Amount of *B. subtilis* Per Carrier

Transfer an inoculated and dried, but unexposed glass cover slip to 10 ml neutralizing recovery medium. Mix on a vortex mixer for one minute and make serial ten-fold dilutions as 1.0 ml into 9 ml PBS. Transfer 0.5 ml portions of various dilutions to the surface of NA in petri plates. Incubate all plates at 35±2° C. for ≥48 hours. Count colonies of *B. subtilis* and multiply by appropriate dilution factors to determine the number of CFU of *B. subtilis* originally inoculated onto and recovered from a carrier.

Prepare Test Substances

Samples B, C, and D were ready for use in the test with no additional preparation necessary. Formulations were held at ambient temperature.

Exposure Inoculated Carriers to Test Substance

The dried inoculum was covered with 50 µl of test substance using a micro-pipettor and the treated carriers were held at ambient temperature for various exposure times. Carriers were treated at 30 second intervals. Three replicate carriers were treated per product formulation and exposure time.

At the end of the exposure time, the cover slip was carefully transferred to 10 ml of neutralizing recovery medium in a 25×150 mm test tube using flamed forceps. Care was used not to lose any of the disinfectant so everything was transferred to the recovery medium. The contents of the tube were mixed on a vortex mixer for one minute to suspend any surviving *B. subtilis* spores.

Three replicate glass cover slips were tested against Samples B, C, and D at exposure times of 1.0, 2.0, 3.0, and 5.0 minutes at ambient temperature.

Recover Surviving *B. subtilis* Spores from Carriers

Make three serial ten-fold dilutions of the medium containing treated carriers as 1.0 ml into 9 ml PBS. Transfer 0.5 ml of each dilution and the medium containing treated carrier to the surface of NA in petri plates. Filter the contents of the tube containing treated carriers through sterile 0.45 membrane filters. Rinse the filter with about 50 ml sterile deionized water (SDIW) and place onto NA in a petri plate. Incubate all plates at 35±2° C. for ≥48 hours. Count colonies of *B. subtilis* and multiply by appropriate dilution factors to determine the number of surviving colony forming units (CFU) of *B. subtilis* per carrier at each exposure time and for each disinfectant formulation.

Validate Neutralization of Test Substances

Add 50 µl of test substance to 10 ml neutralizing recovery medium and immediately spike with approximately 25-50 CFU of *B. subtilis* in 0.1 ml of broth. Mix and hold for 10 minutes at ambient temperature. Do this twice for each formulation. As a comparative viability control, spike two tubes of 10 ml neutralizing recovery medium and two tubes of 9 ml PBS with approximately 25-50 CFU of *B. subtilis* in 0.1 ml of broth. Mix and hold for 10 minutes at ambient temperature. Filter all tubes through sterile 0.45 μm membrane filters. Rinse the filters with about 50 ml SDIW and place onto NA in petri plates. Incubate all plates at 35±2° C. for ≥48 hours. Similar numbers of B. subtilis colonies on neutralization and viability plates validated neutralization of the test formulations and viability of B. subtilis in the media.
Results

| Sample | Exp. Time | Replicate | Surviving CFU | $Log_{10}$ Kill |
|---|---|---|---|---|
| Sample B | 1.0 min | 1 | 0 | 6.10 |
|  |  | 2 | 6 | 5.35 |
|  |  | 3 | 100 | 4.10 |
|  | 2.0 min | 1 | 143 | 3.95 |
|  |  | 2 | 2 | 5.80 |
|  |  | 3 | 0 | 6.10 |
|  | 3.0 min | 1 | 7 | 5.26 |
|  |  | 2 | 0 | 6.10 |
|  |  | 3 | 0 | 6.10 |
|  | 5.0 min | 1 | 1 | 6.10 |
|  |  | 2 | 0 | 6.10 |
|  |  | 3 | 0 | 6.10 |
| Sample C | 1.0 min | 1 | 0 | 6.10 |
|  |  | 2 | 0 | 6.10 |
|  |  | 3 | 0 | 6.10 |
|  | 2.0 min | 1 | 1 | 6.10 |
|  |  | 2 | 0 | 6.10 |
|  |  | 3 | 0 | 6.10 |
|  | 3.0 min | 1 | 0 | 6.10 |
|  |  | 2 | 0 | 6.10 |
|  |  | 3 | 0 | 6.10 |
|  | 5.0 min | 1 | 0 | 6.10 |
|  |  | 2 | 0 | 6.10 |
|  |  | 3 | 0 | 6.10 |
| Sample D | 1.0 min | 1 | 0 | 6.10 |
|  |  | 2 | 0 | 6.10 |
|  |  | 3 | 0 | 6.10 |
|  | 2.0 min | 1 | 0 | 6.10 |
|  |  | 2 | 0 | 6.10 |
|  |  | 3 | 0 | 6.10 |
|  | 3.0 min | 1 | 0 | 6.10 |
|  |  | 2 | 0 | 6.10 |
|  |  | 3 | 0 | 6.10 |
|  | 5.0 min | 1 | 0 | 6.10 |
|  |  | 2 | 0 | 6.10 |
|  |  | 3 | 0 | 6.10 |

Discussion: Sample B with 8.8:1 molar ratio of $H_2O_2$:glycine demonstrated good sporicidal efficacy demonstrating a 5 minute 6 $log_{10}$ kill. However with increased glycine concentrations, samples C (4:1 molar ratio of $H_2O_2$:glycine) and sample D (2:1 molar ratio $H_2O_2$:glycine) were able to penetrate the dried serum and achieve a 6 $log_{10}$ kill in 60 seconds.

As illustrated by these results, the increased concentration of the aminocarboxylic acid (glycine) dramatically enhanced the microbiocidal efficacy of the hydrogen peroxide and peroxyacetic acid disinfectant solution.

Increasing the concentration of alpha aminocarboxylic acid (glycine) in the composition substantially accelerated the kill rate of spores embedded in dried soil. While the concentration of peracetic acid, hydrogen peroxide and Stepfac 8180 in samples B and C were the same, increasing the concentration of glycine from 1% to 2.2% substantially increased the penetration of the dried soil and kill rate of the spores. Further increasing the concentration of alpha aminocarboxylic acid in sample D eliminated the one spore survivor in sample C.

Samples B and D were stored over 1 year and periodically observed. Sample B formed small oily droplets after several weeks of storage. When shaken the oil droplets quickly dispersed forming a hazy solution. However, sample D remained hazy and homogenous throughout the storage period. No oily droplets or separation were observed. The higher concentration of glycine appeared to stabilize the solution. Without being bound by a specific theory, it is believed the alpha aminocarboxylic acid (glycine) forms associations with the peroxycarboxylic acid (peroxyacetic acid). With lower concentrations of glycine the associations separate out of solution by forming oily droplets, while at higher concentrations of glycine, the associations (and/or adducts) formed remain effectively dispersed.

Enhanced Equilibrium

Concentrated peroxyacetic acid was produced by combining 8 ml of 50% $H_2O_2$ with 8 ml of acetic anhydride and mixed using a magnetic stirrer for 6 hours.

Sample 1 was prepared by combining 8 ml of 50% $H_2O_2$ (0.1176 moles), 1.84 gm of 98% $H_2SO_4$, 3.62 gm acetic acid (0.0588 moles) and 83.5 ml of distilled water.

Sample 2 was prepared by combining 8 ml of 50% $H_2O_2$ (0.1176 moles), 1.84 gm of 98% $H_2SO_4$, 4.41 gm glycine (0.0588 moles) and 82.7 ml of distilled water.

Both sample 1 and 2 were treated with 3 ml of the concentrated peroxyacetic acid, mixed and tested for peroxyacetic acid. Samples 1 and 2 measured >6000 ppm but <8000 ppm as PAA. The samples were stored in a dark cabinet for 4 days to allow equilibrium to be reached. After 4 and 7 days the samples were tested again. Sample 1 consistently measured >2000 ppm but <4000 ppm. Sample 2 measured >6000 ppm but <8000 ppm on both days.

Sample 3 was prepared by combining 8 ml of 50% $H_2O_2$ (0.1176 moles), 1.84 gm of 98% $H_2SO_4$, 8.82 gm glycine (0.1176 moles) and 78.3 ml of distilled water. 3 ml of peroxyacetic acid from the stock solution was added and mixed. The sample was tested providing >8000 ppm but <10,000 ppm as PAA. The sample was stored in a dark cabinet for 8 days and again tested measuring >6000 ppm but <8,000 ppm.

The molar ratio of acetic acid and glycine in sample 1 and 2 respectively were the same. However, sample 2 comprising glycine retained the original concentration of peroxycarboxylic acid even in dilute solution where sample 1 comprising acetic acid resulted in substantially reduced levels of peroxyacetic acid.

Discussion of Testing Results and Benefits

The test results clearly demonstrate the addition of alpha aminocarboxylic acid provides a synergistic effect to the composition by: forming associations with the peroxycarboxylic acid that enhances the equilibrium product of the peroxycarboxylic acid, accelerates the penetration of dried soil deposits, and enhances the microbiocidal efficacy of the composition.

The associations formed between the alpha aminocarboxylic acid, peroxycarboxylic acid and/or hydrogen peroxide substantially accelerate the rate of kill of spores embedded in dried soil resulting in enhanced microbiocidal efficacy of the composition. While peracetic acid is in many formulations that demonstrate excellent microbiocidal efficacy against spores in suspensions as illustrated, the ability of these compositions to effectively kill spores embedded in dried soil deposits is greatly compromised. The disclosed invention overcomes a significant hurdle in preventing disease transfer in hospitals and other critical care institutions.

DETAILED DESCRIPTION OF PREFERRED EMBODIMENTS

As used herein, "alpha aminocarboxylic acids" also "aminocarboxylic acids" comprise zwitterionic compounds having an amine functional group attached to the alpha carbon of a carboxylic acid and have the general structure:

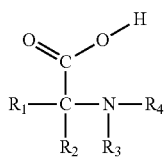

Wherein $R_1$, $R_2$, $R_3$, and $R_4$ comprise hydrogen (H) or carbon (C).

The amine group attached to the alpha carbon has a corresponding and dedicated carboxylic acid group. The aminocarboxylic acids structure substantially increases the electronegativity to the corresponding carboxylic acid group reducing the pKa value of the carboxylic acid group to less than 3.0. The aminocarboxylic acids comprise a carboxylic acid having a carbon based backbone ranging from C1 to C6. The carbon based backbone may comprise an aliphatic or cyclic structure. The carbon based backbone of the aminocarboxylic acids can be substituted with other groups. Non-limiting examples of substitution groups include alkyl, aryl, cyclic, heterocyclic, halo, amine, nitro, keto, carboxyl, and hydroxyl. The molecular mass of the aminocarboxylic acids is preferably less than 200 to enhance its penetration of membranes of microbiological organisms.

Aminocarboxylic acids are a family of compounds that often possess substantially different properties. For example, ethylenediaminetetraacetic acid (EDTA) possesses 4 carboxylic acid groups and 2 amine groups, resulting in a stoichiometric ratio of 1:2 amine to carboxylic acid respectfully. Since the amine groups is not in stoichiometric balance with the carboxylic acid groups, the carboxylic acid groups have a range of pKa values reported as $pK_1$=2.00, $pK_2$=2.65, $pK_3$=6.18, and $pK_4$=10.30. Therefore EDTA does not represent a suitable aminocarboxylic acid for use in the disclosed invention for purposes of killing microorganisms, but may be used as a chelating agent to inhibit decomposition of the solution resulting from metal catalyst.

Peroxycarboxylic acid is an equilibrium product between the parent carboxylic acid and hydrogen peroxide on the one side of the equilibrium equation, and the equilibrium products comprising peroxycarboxylic acid and water on the other side of the equation. Because of the equilibrium, producing peroxycarboxylic acid from concentrated reagents results in higher conversion and higher concentrations of peroxycarboxylic acids. However, when the concentrated solution is diluted to produce a ready-to-use (RTU) solution and stored, the equilibrium shifts some portion of the peroxycarboxylic acid back to the parent carboxylic acid and hydrogen perioxide to achieve the new equilibrium. It has been discovered that treating the solution with aminocarboxylic acid preserves or substantially retains the concentration of peroxycarboxylic acid in the original solution prior to establishing equilibrium.

This unexpected result allows for solutions with elevated peroxycaroboxylic acid activity, and/or lower acetic acid concentrations in peroxyacetic acid containing solutions thereby reducing the offensive odor.

As used herein, "equilibrium enhanced" also "enhanced equilibrium" describes a solution of the invention comprising alpha aminocarboxylic acid in sufficient concentration to sustain a concentration of peroxycarboxylic acid at least 25% higher than a comparable solution having a molar equivalent of the parent carboxylic acid when it has reached its peroxycarboxylic acid equilibrium. The addition of alpha aminocarboxylic acid in an effective concentration provides for a higher concentration of peroxycarboxylic acid for an extended period of time.

Forming an RTU (Ready to Use) solution from a concentrate provides extended periods of elevated concentrations of peroxycarboxylic acid resulting from the enhanced equilibrium provided by the associations even after the concentrated solution has been diluted for a period that exceeds the time required for peroxycarboxylic acid equilibrium to be achieved. This can be extremely beneficial were sterilization is required such as medical instruments and contaminated rooms.

The solution having equilibrium enhanced concentration of alpha aminocarboxylic acid has a concentration of peroxycarboxylic acid at least 25% higher than the equilibrium concentration of peroxycarboxylic acid in a comparable solution that is not treated with an effective concentration of aminocarboxylic acid. For example, a solution prepared by combining 8 ml of 50% $H_2O_2$ (0.1176 moles), 1.84 gm of 98% H2SO4, 3.62 gm acetic acid (0.0588 moles) and 83.5 ml of distilled water and originally treated with approximately 6000 ppm of peroxyacetic acid will achieve a new equilibrium during storage resulting in approximately 2000 ppm of peroxyacetic acid. However, a solution prepared by combining 8 ml of 50% $H_2O_2$ (0.1176 moles), 1.84 gm of 98% H2SO4, 4.41 gm glycine (0.0588 moles) and 82.7 ml of distilled water and originally treated with 6000 ppm of peroxyacetic acid retained greater than 75% of the original concentration (>4500 ppm) of peroxyacetic acid for a period of time exceeding the time required for the solution having no alpha aminocarboxylic acid to reach equilibrium.

As used herein, "association" also "associations" describes the formation of complexes formed between the aminocarboxylic acid and percarboxylic acid and/or hydrogen peroxide. The associations enhance the microbiocidal efficacy by accelerating the rate of penetration of dried soil deposits and microbiological organisms (e.g. spores), as well as enhance the equilibrium of the peroxycarboxylic acid. The alpha aminocarboxylic acid forms associations with at least one of peroxycarboxylic acid and hydrogen peroxide.

As used herein, "association forming concentration of alpha aminocarboxylic acid" is the concentration of alpha aminocarboxylic acid in the composition necessary to form associations between the aminocarboxylic acid and peroxycarboxylic acid and/or hydrogen peroxide, and provide enhanced microbiocidal efficacy and can enhanced equilibrium of the peroxycarboxylic acid. The preferred concentration of aminocarboxylic acid is sufficient to achieve a molar ratio of hydrogen peroxide to aminocarboxylic acid from about 8:1 to 0.5:1 respectively. Forming an RTU (Ready to Use) solution from a concentrate provides extended periods of elevated concentrations of peroxycarboxylic acid which are extremely beneficial were sterilization is required such as medical instruments and contaminated rooms.

As used herein, "enhanced microbiocidal efficacy" describes the ability of the associations formed in the microbiocidal composition to accelerate the rate of kill of microbiological organisms (e.g. spores) embedded in dried soil when compared to formulations having comparable concentrations of peroxycarboxylic acid without the alpha aminocarboxylic acid. Microbiocidal compositions comprising an association forming concentration of alpha aminocarboxylic acid reduce the time required to penetrate and kill microbiological organisms (e.g. spores) embedded in dried soil. The microbiocidal composition of the invention comprising an association forming concentration of alpha aminocarboxylic acid can provide a 6 $\log_{10}$ kill of bacterial spores embedded in dried soil at least 2× (2 times) faster, preferably at least 3× faster, and most preferred at least 4× faster than a microbiological composition comprising the comparable concentrations of the same ingredients but void of the association forming concentration of alpha aminocarboxylic acid.

As used herein, "pH of the solution being less than the isoelectric point of the aminocarboxylic acid" is used to describe the pH of the solution to induce formation of at least some portion of cationic charged species of the aminocarboxylic acid. The isoelectric point (pI) value takes into account the pKa value of the carboxylic acid and the pKb value of the amine(s) comprising the zwitterionic aminocarboxylic acid and is the pH value at which the aminocarboxylic acid possesses no net charge at 25° C. The amount of acid added to the solution must provide enough excess free hydrogen ion to achieve a pH of less than the pI value of the zwitterionic aminocarboxylic acid. At a pH below the pI value at least a portion of the aminocarboxylic acid begins taking on a net positive (cationic) charge. The excess hydrogen ions may also catalyze the reaction by activating the acyl carbon which then undergoes nucleophilic substitution with the hydrogen peroxide. The amount of acid required will vary depending on the zwitterionic equilibrium of the aminocarboxylic acid. Non-limiting examples of aminocarboxylic acids and their respective reported isoelectric point values (pI) at 25° C. include: alanine (6.11), aspartic acid (2.98), glycine (6.06), glutamic acid (3.08) and arginine (10.76). Furthermore, the amount of acid required to achieve the desired pH also depends on whether the acid form or salt form of the aminocarboxylic acid is used, the type of acid used, the speed of the reaction, and the desire to stabilize the peroxide solution. Generally the pH of the solution ranges from about 0.6 to 7.0, preferably 1.0 to 6, and most preferred 1.5 to 5.0. In the case where two or more aminocarboxylic acids comprise the solution, the pH can be adjusted to achieve the lowest pI value, an average pI value, or the highest pI value of the aminocarboxylic acids comprising the solution.

As used herein, "soil" comprises an organic and inorganic matrix that when mixed with bacterial spores and dried forms a solid deposit that impedes the contact between peroxyacetic acid and bacterial spore. One non-limiting example of a synthetic soil used for testing comprises a mixture of the following stock solutions in phosphate buffered saline (PBS):

a. 0.5 g Tryptone in 10 ml PBS b. 0.5 g Bovine Serum Albumin (BSA) in 10 ml PBS c. 0.04 g Bovine Mucin in 10 ml PBS As used herein, "microorganisms" is a general term used to describe the type of microbiological organisms killed by the solutions of the invention. Non-limiting examples of microorganisms include endospores, mycobacterium, bacteria, virus, mold, and fungi.

As used herein "food processing systems" refers to the surfaces of equipment and surroundings used to process food. Food processing systems includes the equipment and building structures used to process, produce, store, wash, move, sanitize, cut, and package consumable food items.

As used herein, "hard surfaces" include: countertops; floors; walls; tables; cabinets; doors; doorknobs; hand railings; toilets; sinks; faucets; food processing equipment, and the like. Hard surfaces are found in industrial and institutional facilities including hospitals, medical clinics, food processing facilities, day care centers, nursing homes, cafeterias, Universities, schools, and the like.

As used herein, the phrase "health care equipment" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the phrases "medical instrument", "dental instrument", "medical device", "dental device", "medical equipment", or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthoscopes) and related equipment, and the like, or combinations thereof.

The present invention is intended to provide a rapid-acting hydrogen peroxide-based liquid disinfectant containing low levels of active ingredients. Some embodiments are suitable for high level disinfection. In this context, "high level disinfection" means the destruction of mycobacterium species as well as bacterial endospores to the degree required in semicritical and critical applications, as measured by standard carrier testing methods.

Solutions according to the present invention are effective disinfectants and sporicidal, are low in toxicity and employ biodegradable ingredients. The result is a disinfectant which does not suffer from the occupational safety or environmental disposal problems associated with current technologies. Because of the low levels of hydrogen peroxide and other supplemental ingredients, "in use" solutions according to the present invention exhibit very low reactivity towards material substrates and tissue, and are therefore non-corrosive to skin or metals.

The solution may be used in the disinfection of semicritical and critical surfaces and/or instruments, as well as noncritical surfaces where use of an anti-tuberculosis disinfectant is recommended. Such a disinfectant is common in the dental industry and in health care settings for disinfecting respiratory equipment. A major field of application is in the processing of delicate surgical instruments and devices, including flexible endoscopes. The rather mild, non-reactive nature of the components in the mixture, and the low levels at which they are formulated, make the solution ideal for the processing of flexible medical devices, while at the same time ensuring complete disinfection, even in the presence of organic matter.

Without being bound by theory, it is believed hydrogen peroxide and peroxycarboxylic acid form associations with the aminocarboxylic acid that enhances the microbicidal efficacy of the composition. The hydrogen peroxide and peroxycarboxylic acid form associations with the electronegative aminocarboxylic acids through hydrogen bonding thereby improving the adsorption onto and/or absorption through the membranes of the microorganisms.

The aminocarboxylic acids of the invention are zwitterionic and their respective charge distribution varies based on the specific aminocarboxylic acid and the pH of the solution. When the solutions of the invention are within the preferred pH range for a given aminocarboxylic acid, a portion of the equilibrium product will be cationic and another portion will be neutral in charge. Cationic charged APOCA have increased affinity toward exposed anionic charges on the microorganism cell membrane, whereas the neutral charged APOCA has an increased Log P (octanol-water partition) resulting in increased rate of absorption through the cell membrane. Once through the cell membrane disruption of the vital organs within the cytoplasm take place. The zwitterionic properties are also believed to enhance permeation through the porins of mycobacterium thereby accelerating penetration and inactivation of the mycobacterium.

The oxidizing power of peroxide represented by RO—OH where R is Hydrogen or a Carbon based backbone shows an inverse relationship with the pKa of the leaving group RO—. Thus, $H_2O_2$ is much less reactive than $CH_3CO_3H$. In general electron-withdrawing groups on the —$CO_3H$ moiety markedly increase the rate of oxygen atom transfer. Peroxyacetic acid has a reported pKa of 4.76 and is an effective microbiocide and is known to effectively inactivate endospores. For comparative purposes aminoethanoic acid (glycine) has a reported pKa of 2.34, and pyrrolidine-2-carboxylic acid pKa is 1.99. Furthermore, the nitrogen having greater electronegativity than carbon enhances the formation of the peroxyacid. The preferred aminocarboxylic acids have a pKa of the leaving group of less than 3.0.

The hydrogen peroxide used in the present solution is typically a commercially available aqueous solution, usually in a concentration of 10-50% w/w. Commercial solutions for hydrogen peroxide may contain additional stabilizers and additives as are known in the art. In the present inventive solution, the preferable concentrations of hydrogen peroxide ranges from about 0.1% to about 6% w/w and more preferably from about 1.0% to about 5% w/w. While solutions with higher concentrations of hydrogen peroxide can be advantageously used, they are typically highly corrosive and have material compatibility problems. Thus, they cannot be applied in practice for the disinfection of delicate instruments. They can also be hazardous and associated with occupational safety and shipping restrictions.

It is recognized that the above specified low levels of hydrogen peroxide can be achieved by dilution of a more concentrated stock solution. Moreover, a dry particulate composition may be formulated for mixing with water by an end user to produce a solution according to the present invention. Hydrogen peroxide is commercially available in a dry form as persalt compounds, of which the preferred ones are sodium percarbonate and sodium perborate in its monohydrate and tetrahydrate forms. Since sodium percarbonate contains about 20% equivalent hydrogen peroxide by weight, and sodium perborate monohydrate and tetrahydrate contain about 30% and 20% respectively by weight, proper allowance must be made when blending the dry mixture of components to achieve the desired levels of hydrogen peroxide upon dissolution in water.

Solutions according to the present invention comprise peroxycarboxylic acid. The peroxycarboxylic acid may be selected from at least one $C_1$ to $C_{21}$ carbon based peroxycarboxylic acids and/or aminoperoxycarboxylic acids.

Aminoperoxycarboxylic acids comprise the equilibrium products resulting from the reaction between hydrogen peroxide and at least one aminocarboxylic acid and aminocarboxylic acid precursors. Non-limiting examples of aminocarboxylic acid precursors include aminocarboxylic: anhydrides, amino aldehydes, and amino acyl chlorides. Non-limiting examples aminoperoxycarboxylic acids include aminoperoxyethanoic acid and 2-aminoperoxypropanoic acid.

The preferred method of producing aminoperoxycarboxylic acid is to combine an aminocarboxylic acid precursor exemplified by glycine anhydride to a solution of hydrogen peroxide and allowing the mixture to react while mixing. The molar ratio of reactants should be from about 1.5:1 to 10:1 based on hydrogen peroxide to the aminocarboxylic acid respectfully. The $C_1$ to $C_{21}$ carbon based peroxycarboxylic acids may be aliphatic or cyclic carbon structures. Non-limiting examples of $C_1$ to $C_{21}$ carbon based peroxycarboxylic acids include: peroxyacetic acid, peroxybutanoic acid, peroxypentanoic acid, peroxysuccinic acid, peroxybenzoic acid, peroxyoctanoic acid, peroxyadipic acid, peroxydodecanoic acid, and peroxydecanoic acid. Preferably the concentration of hydrogen peroxide is about 2 to 30 w/w % based on the total weight of the mixture. The resulting solution comprising aminoperoxycarboxylic acid can be diluted after production or combined with other additives to produce the solutions of the invention.

An alternative method for producing aminoperoxycarboxylic acid comprises adding a catalytic amount of free hydrogen ions to a solution comprising hydrogen peroxide and aminocarboxylic acid. The excess hydrogen ions catalyze the reaction by activating the acyl carbon which then undergoes nucleophilic substitution with the hydrogen peroxide. When acid forms of the aminocarboxylic acid are used, the amount of acid required provide sufficient amount to supply the amine functional group with some excess free hydrogen ions to catalyze the reaction. The solution may be heated to about 100 to 120° F. to further accelerate the reaction. It is desirable not to over acidify or over heat as decomposition of the aminoperoxycarboxylic acid may occur.

The $C_1$ to $C_{21}$ carbon based peroxycarboxylic acids may be produced using similar methods as those described for producing aminoperoxycarboxylic acids using the respective carbon based carboxylic acid or precursor. Peroxyacetic acid can also be purchased commercially for use in the solution. FMC Corporation is a commercial supplier of peroxyacetic acid.

Solutions according to the present invention also contain at least one component chosen from aminocarboxylic acids. Aminocarboxylic acids can be un-substituted or substituted. Non-limiting examples of un-substituted aminocarboxylic acids include glycine, and alanine. Non-limiting examples of aminocarboxylic acid substitution groups include alkyl, aryl, cyclic, heterocyclic, halo, amine, nitro, keto, carboxyl, and hydroxyl. Non-limiting examples of substituted aminocarboxylic acids include methionine, phenylalanine, tyrosine, and glutamine.

Amino acids are preferred zwitterionic aminocarboxylic acids. Examples of preferred amino acids include: glycine, proline, alanine, arginine, lysine, aspartic acid, glutamic acid, serine, threonine, asparagines, glutamine, valine, isoleucine, leucine, phenylalanine, tyrosine, and tryptophan.

Solution according to the present invention may also contain benzyl alcohol, in a concentration of from 0.01 to 8% w/w or from 0.01 to 4% w/w of the total solution. Benzyl alcohol occurs naturally in essential oils of vegetable origin. Commercially, benzyl alcohol is commonly manufactured from the reaction of benzyl chloride and sodium carbonate. Benzyl alcohol is used as a photographic developer for color movie film and in perfumes, flavour industries, pharmaceuticals as a bacteriostatic, cosmetics, ointments, emulsions, textiles, sheet plastics and inks. Benzyl alcohol has a vapor pressure lower than 0.1 mmHg (at 20 degrees C.) which meets the standards of CARB California Air Resources Board for volatile organic compounds.

If inactivation of hydrophilic viruses is desired, the solution may contain at least one C6-C12 alkyl diphenyl oxide sulfonate surfactant (e.g. alkyl diphenyl oxide disulfonate surfactant). This ingredient has been found to not only impart hydrotroping and detersive properties to the mixture, but also, surprisingly, to play a key role in the inactivation of difficult to mitigate hydrophilic viruses. The inclusion of this ingredient is believed to provide the necessary broad activity spectrum of a tuberculocidal product. Examples of this ingredient are the alkyl diphenyl oxide disulfonate surfactants manufactured commercially by the Dow Company in association with the trademark DowFax. The preferred concentration of this ingredient is from 0.05 to 3.0% w/w of the solution.

The solution may also contain from 0.005 to 3.0% w/w of at least one nonionic surfactant chosen from the family of ethoxylated alcohols and alkylglycosides of hydrophile lyophile balance between 5.0-15.0, or from the group of sufficiently water-soluble block copolymers of ethylene oxide or propylene oxide. These ingredients impart low surface tension to the solution, improving its wetting and detergency properties. These surfactants are stable in the presence of acid hydrogen peroxide media, and do not contribute to excessive hydrogen peroxide decomposition. They are available commercially from numerous manufacturers. Examples include surfactants sold in association with (a) the trademark Alfonic by Condea Vista, (b) the trademark Tergitol by Dow Chemical, (c) the trademark Pluronic and Tetronic by BASF, and (d) the trademark Makon by Stepan. The solution may also contain at least one anionic surfactant chosen from C8-C16 alkyl benzene sulfonic acids and alkali metal, alkaline earth metal, ammonium or alkylamine salts thereof, C8-C18 alkyl sulfonic acid, or C8-C16 alkyl ethoxylated or non ethoxylated sulfates, in a concentration of from 0.01 to 5.0% w/w of the mixture. These ingredients help impart detersive properties to the solution, and are particularly useful if the solution is used in a cleaning step prior to formal disinfection. These ingredients are available commercially from many vendors. Examples include products sold in association with the trademarks Biosoft and Stepanol by Stepan and the trademark Hostapur by Hoechst.

Chelating agents may be included in the solution of the invention to enhance cleaning performance and stability of the solution. Examples include 1-hydroxyethylidene-1,1-diphosphonic acid sold commercially by Solutia in association with the trademark Dequest 2010, and aminotrimethylene phosphonic acid sold commercially by Allbright and Wilson in association with the trademark Dequest 2010. Polycarboxylate chelators may be employed. Examples include ethylenediaminetetraacetic acid, hydroxyethyl-ethylenediaminetriacetic acid, 2-hydroxyethyl-iminodiacetate (HEIDA) and nitrilotriacetic acid. Chelating agents aid the detergency process by sequestering cationic species responsible for the inactivation of anionic surfactants by cation-anion coupling, by increasing the zeta potential between substrates and soil particles, and by dissolving larger soil aggregates held together by cation bridging.

Other ingredients which are sufficiently stable in the presence of hydrogen peroxide, and at the acid conditions of the present solution may be added to impart desirable qualities. Suitable dyes and fragrances may be employed for modifying the color and odor of the solution. Preferred fragrance comprises dihydro myrcenol. Thickening agents may be added to modify its Theological properties. Corrosion inhibitors may also be added provided they are compatible with hydrogen peroxide in an acid medium and do not adversely affect the germicidal properties of the solution. Such ingredients include, but are not limited to, benzotriazoles, tolutriazoles, sodium nitrite, and sodium molybdate.

Solutions of the present invention can be readily prepared by serial addition of the above-mentioned ingredients to deionized water. For optimum product stability, the water should have an electrical conductivity of less than 200 micromhos. Water purified by ion exchange or reverse osmosis is suitable for this purpose. Generally the first ingredient(s) to be added to the required amount of water is the hydrogen peroxide preferably followed by the aminocarboxylic acids. These dry solid ingredients are not highly soluble and therefore require more time to dissolve than the other ingredients. About 90% of the final water content of the solution is added to a mixing vessel made of high density polypropylene or passivated austenitic stainless steel, and equipped with a stirrer with shaft and blades constructed of these same materials. Once thoroughly mixed, acid should be added to reduce the pH below the isoelectric point of the aminocarboxylic acid. The amount of acid should be sufficient to stabilize the hydrogen peroxide solution and peroxycarboxylic acid. After allowing sufficient time to mix (e.g. between 0.5 to 1 hr), the rest of the ingredients can be added serially in no particular order. If the peroxycarboxylic acid is to be produced in the same vessel, it is preferred that the hydrogen peroxide be respective precursors be added and the pH adjusted to promote the formation of peroxycarboxylic acid allowing sufficient time to react (about 1 to 6 hours depending on temperature) before addition of surfactants, hydrotropes and other additives that are applicable. Final pH adjustment if any can be made prior to completion of the mixing to further stabilize the solution to improve shelf storage.

As mentioned above, the present solutions are suitable for the disinfection of delicate and chemically sensitive materials with minimal occupational safety risks. Some embodiments of the present invention are particularly useful in the disinfection of semi-critical and critical surfaces and instruments in the health care, veterinary care and dental care industries. Specific applications include, but are not limited to, the cleaning and disinfection of invasive and non-invasive surgical equipment, the cleaning and disinfection of rigid and flexible invasive and non-invasive diagnostic equipment, the cleaning and disinfection of prostheses and implants, the internal cleaning and disinfection of body fluids recirculating machinery, and the cleaning and disinfection of non-critical surfaces where the use of products with tuberculocidal efficacy is recommended, such as dental chairs and respiratory resuscitation equipment.

The methods of application of the present disinfecting solution include, but are not limited to, spraying the solution on the surface to be treated with a spraying trigger or nozzle, simply wetting the area or instrument with the solution, filling an enclosed space (a tube for example) with the solution and allowing the solution to sit there for the required contact time, and circulating the solution through internal conduits and passages of an instrument for a predetermined period of time. The solution can be applied at room temperature or at another temperature (i.e. from 4 .degree. C. to as high as 70 .degree. C.).

When the present invention is prepared as a dry mixture, the above mentioned application methods can still be used; however, the dry mixture must first be dissolved in water to produce the present aqueous solution. Preparation of the present aqueous solution may be done in-situ or just prior to use, either manually or automatically in a washing disinfection machine equipped for handling powders.

Veterinary

The disinfecting solution of the invention can be applied to agricultural or veterinary objects or surfaces include animal feeds, animal watering stations and enclosures, animal quarters, animal veterinarian clinics (e.g. surgical or treatment areas), animal surgical areas, and the like.

The foregoing examples are for illustrative purposes only and shall not be construed so as to restrict the scope of the invention as defined by the following claims.

I claim:

1. A method for killing microbiological organisms embedded in a dried soil deposit, said method comprising the steps of: forming a composition comprising; an aqueous solution of hydrogen peroxide in a concentration from 3% to 6% by weight, an association forming concentration of glycine having a molar ratio of hydrogen peroxide to glycine from about 8:1 to 0.5:1 respectively, peroxycarboxylic acid in a concentration from 0.05% to 1% by weight, a phosphate ester in a concentration from 0.05-1% by weight comprising a hydrophilic polyoxyethylene chain having a range of PEO-3 to PEO-9 and an R-terminal group selected from the group consisting of a lipophilic alkyl chain having a range of $C_9$ to $C_{13}$ and a nonylphenol, the pH of the composition being less than the isoelectric point of the glycine; wherein the glycine forms associations with at least one of peroxycarboxylic acid and hydrogen peroxide; said associations provide enhanced microbiocidal efficacy, and applying the composition to said deposit.

2. A method of claim 1, wherein the microbiological organisms comprise spores.

3. A method of claim 1, wherein the microbiological organisms comprise mycobacterium.

4. A method of claim 1, wherein the composition is applied in the form of a fabric wipe.

5. A method of claim 1, wherein the pH of the aqueous solution is 1.5 to 4.0.

6. A method for killing, microbiological organisms embedded in a dried soil deposit, said method comprising the steps of: diluting a concentrate having up to 30% by weight hydrogen peroxide in water to produce a composition in the form of an aqueous solution, the composition comprising: hydrogen peroxide in a concentration from 3% to 6% by weight, an association forming concentration of glycine having a molar ratio of hydrogen peroxide to glycine from about 8:1 to 0.5:1 respectively, peroxycarboxylic acid in a concentration from 0.05% to 1% by weight, a phosphate ester in a concentration from 0.05% to 1% by weight comprising a hydrophilic polyoxyethylene chain having a range of PEO-3 to PEO-9 and an R-terminal group selected from the group consisting of a lipophilic alkyl chain having a range of $C_9$ to $C_{13}$ and a nonylphenol, the pH of the composition being less than the isoelectric point of the glycine: wherein the glycine forms associations with at least one of peroxycarboxylic acid and hydrogen peroxide, said associations provide enhanced microbiocidal efficacy: wherein the composition has enhanced equilibrium and maintains enhanced microbiocidal efficacy for at least 7 days, and applying the composition to said deposit.

* * * * *